United States Patent [19]

Ferrara

[11] Patent Number: 4,487,696
[45] Date of Patent: Dec. 11, 1984

[54] BLOOD SEPARATOR AND DISPENSER

[76] Inventor: Louis T. Ferrara, 2988 Ave. T, Brooklyn, N.Y. 11229

[21] Appl. No.: 915,530

[22] Filed: Aug. 14, 1978

[51] Int. Cl.² ............................................. B01D 33/22
[52] U.S. Cl. .................................. 210/399; 210/515; 210/516; 210/DIG. 24
[58] Field of Search ............. 128/DIG. 5, 2 F, 218 P; 23/258.5, 259; 210/516, DIG. 23, DIG. 24, 399, 323 R, 359, 324, 340, 341, 348, 359, 390, 398, 399, 419, 420, 435, 436, 472, 398

[56] References Cited

U.S. PATENT DOCUMENTS

| | | | |
|---|---|---|---|
| 3,355,098 | 11/1967 | Farr | 210/540 |
| 3,481,477 | 12/1969 | Farr | 210/DIG. 23 |
| 3,493,503 | 2/1970 | Mass | 210/DIG. 23 |
| 3,586,064 | 6/1971 | Brown et al. | 210/540 |
| 3,706,305 | 12/1972 | Berger et al. | 210/DIG. 23 |

Primary Examiner—Frank Sever

[57] ABSTRACT

A serum and cell separating and dispensing device comprising an elongated tubular vessel partitioned throughout its length forming two distinct compartments containing vent orifices on either side. One opened end of the vessel is fitted with a resilient element containing a larger and smaller orifice which houses a small and large pore filter respectively. These orifices communicate with the two compartments respectively. At the opposite end of the vessel are two small tubular vessels extending from and communicating with the compartments formed by the partition. Blood drawn in an evacuated collection tube such as Becton Dickinson's vacutainer is centrifuged after clotting. The device is forced into the opened end of the collection tube and pressed downwardly. The resilient element forms an air trap by touching the inner wall of the collection tube and serum is forced through the orifices containing the filters. Due to the pore size of the filters and the size of the orifices, serum and cells become located within the separate compartments. One may tilt the assembly in one direction allowing drops of serum to be dispensed whereas turning the assembly in another direction allows dispensing of cells. In this manner blood samples from patients may be dispensed for crossmatching purposes without using the usual droppers. At the same time integrity of patients identification is maintained.

6 Claims, 4 Drawing Figures

U.S. Patent    Dec. 11, 1984    4,487,696
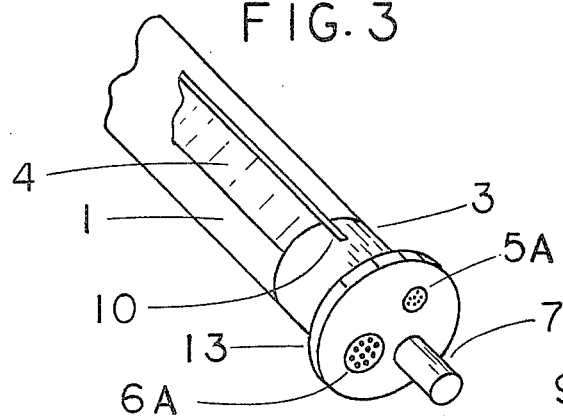
FIG. 3
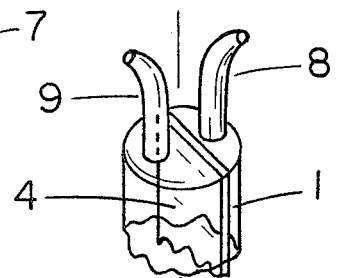
FIG. 4
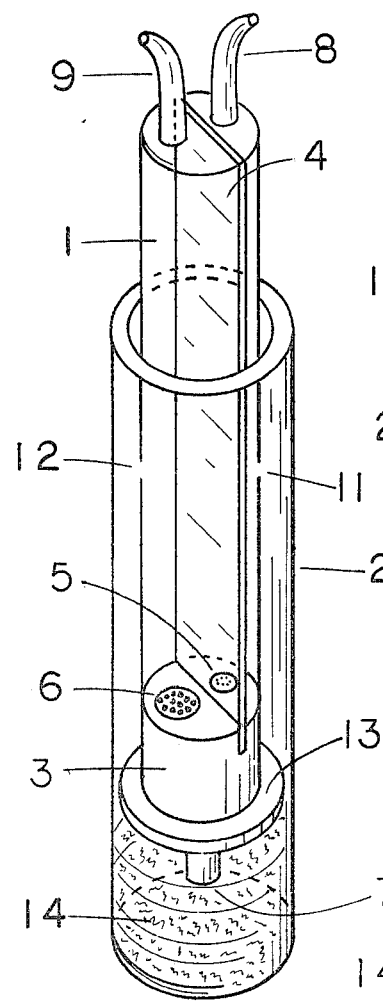
FIG. 1
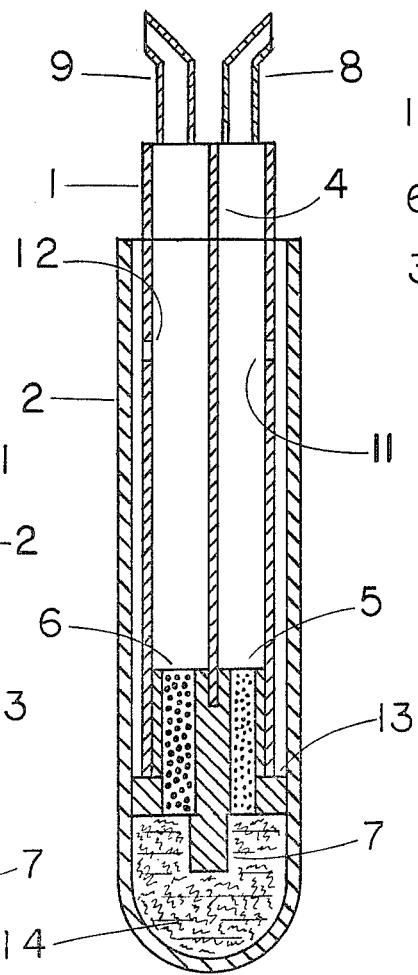
FIG. 2
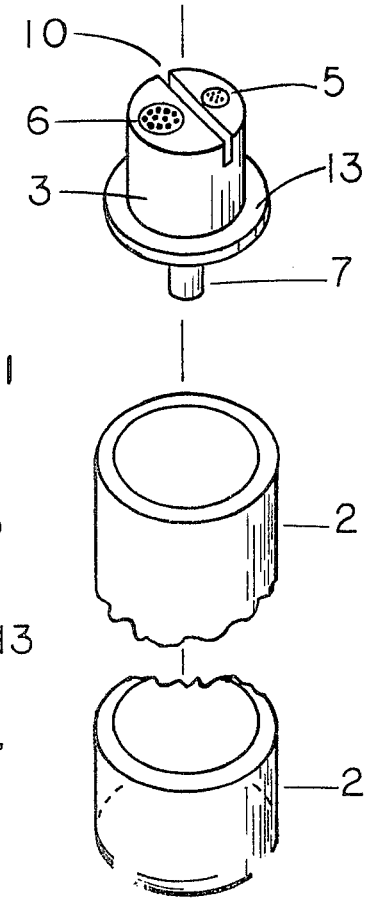

BLOOD SEPARATOR AND DISPENSER

BACKGROUND OF INVENTION

The invention relates to the dispensing in a dropwise manner of serum and cells in the area of blood banking where blood may be typed and crossmatched for a prospective recipient. It is the custom to obtain a sample of blood by using an evacuated blood collection tube in conjunction with a special cannula. After blood is obtained by vena puncture it is allowed to clot within the confines of the collection tube whereby it is subsequently centrifuged for the purpose of separating the serum and cells. After centrifuging, serum is aspirated or poured into a similar container or tube and labeled. During the process of typing and crossmatching this recipients blood, serum and cells are required in various amounts of approximately one to three drops for each determination. For example, a front typing may require three drops of cells to be dispensed, i.e., one drop for each anti-serum on a slide or tube respectively.

In a similar manner serum must also be dispensed for the backtyping procedure and for the crossmatching as well. This is presently being done with a dropper type dispenser pipet. Blood or serum is drawn by the suction of a bulb into the pipet whereby it is subsequently dispensed as described. The use of these squeeze bulb pipets or medicine dropper type dispensers becomes somewhat tedious especially when many typings and crossmatching must be done. There is also the fact that one may have to use the same specimen again and thus require a fresh dispensing pipet.

SUMMARY OF THE INVENTION

It is the object of this invention to provide a means to expedite the separation and dispensing of serum and cells for crossmatching procedures and similar purposes, while at the same time maintaining the integrity of the patients specimen. It is also the object of the invention to provide a device which can separate or segregate serum and cells simultaneously in one vessel which is partitioned in such a manner that serum and cells are directed into these compartments via a special filter system which communicates with said compartments. It is also the object to provide a means of easily dispensing in a dropwise manner each of the blood components namely serum and cells by merely tilting the device or assembly to one side so that drops are dispensed of one component while the other component remains intact in the adjacent compartment. In a similar manner the assembly may be rotated and subsequently tilted to dispense the other component. It is also the object to provide in such a device a means to vent both compartments so as to facilitate the dispensing of the components. It is also the object of the invention to combine filter system, compartment size, vents, and orifice size at the point where components are dispensed so that dispensing can be done in uniform size drops that can be counted and not to leak or run out haphazardly.

DESCRIPTION OF DRAWINGS

FIG. 1 Shows a blood collection tube 2 with the device 1 within. At the bottom of the collection tube is shown a clot which is segregated from the tubular device.

FIG. 2 is an elongated cross sectional view of the collection tube and separator-dispensing device.

FIG. 3 Shows the bottom portion of the device 3 with two orifices 5 and 6 containing filters 5a and 6a.

FIG. 4 an exploded longitudinal view of the tubular device 1 resilient element 3, and collection tube 2.

For a better understanding of the invention herein a description of the preferred embodiment is provided which is shown in FIGS. 1 and 2.

In FIG. 1 the separator-dispensing device comprises; a tubular element 1 separated on the inside by a partition of the same material. At the lower portion of the tubular element is fitted by friction a resilient element 3 which is of an elastomeric material such as rubber. Element 3 has two orifices which extend through its elongated axis as shown in FIGS. 3 & 4. Two filters 5a & 6a with different pore sizes are housed within these orifices. The partition 4 which runs the length of the vessel meets the resilient element 3 at point 10 FIG. 4 thus providing a channel or groove which houses the bottom end of the partition thereby providing a leak proof joint to maintain the integrity of each compartment. The bottom portion of element 3 is provided with a flange 13 which acts as an air seal around the inner walls of the collection tube 2. Beneath this is a tubular shaped extension 7, FIGS. 1 & 3, which acts to keep clot 14 from obstructing the passage of cells through filter 5a. This extension 7 is specifically embodied in the device for the cellular compartment since serum in the serum compartment will initially be forced in its compartment by suction and remain therein. This will become apparent as the operation of the device is described. At the upper portion of tubular element 1 are two small tubular elements 8 & 9 each opened at both ends respectively. One end of these elements communicate with the spaces formed by the partition 4. The other ends respectively have orifices which are opened to the environment and provide exit means for the blood components to be dispensed. Tubular element 1 is provided at a suitable location with vents 11 & 12 respectively.

The system operates as follows. After blood is collected in tube 2, it is allowed to clot and subsequently centrifuged thereby forming a top portion or layer of serum, and a bottom containing clot, loose cells and some serum. The device, element 1, is forced downward into the collection tube FIG. 1. As air becomes entrapped between flange 13 and the bottom of the collection tube it forces serum to penetrate the filters 5a and 6a. Filter 6a is composed of fine pores that allow only serum to pass through. Filter 5a has larger pores but a smaller orifice that houses it, so that serum and cells may pass through and into the compartment it communicates with. When flange 13 reaches the clot the downward motion of element 1 is stopped. At this point there exists serum in both compartments. It should be noted that one compartment, namely the cellular compartment is substantially smaller than the other. This compartment communicates with the smaller orifice containing the large pore filter and will subsequently store cells as well as serum. This compartment is made smaller so that the dilution of cells with serum will not be substantially high. That is to say that the dilution of cells with serum should be approximately 2–5% as is suitable for blood banking purposes.

When the entire assembly, tube 2 containing tubular device 1 is titled in the downward direction of element 9, serum flows in its compartment in that direction. Since the size of the compartment in relation to the amount of serum is substantially much greater, the venting orifice 12 being oriented above the serum allows air to entire the compartment thus allowing serum to be dispensed dropwise through tubular element 9. In a similar manner simultaneously, cells from the adjacent compartment flow in the same direction as the serum towards element 8. However since tubular element 8 is pointing or angled in an upward direction no cells leak out while serum is being dispensed. Likewise, when the entire assembly is rotated so that the tip of element 8 is pointed downward, cells are dispensed dropwise. Vent holes 11 & 12 and the sizes of elements 8 & 9 and including the volume of the compartments are so constructed that drops of serum and cells may be dispensed respectively with ease of control by tilting and the aid of gravity. That is to say that the respective components would not run out haphazardly when the assembly is tilted, but rather each component may be dispensed dropwise, i.e., one drop at a time and as many drops as is necessary for the specific determination i.e., one to three drops, etc. It should be noted that whereas cells and serum are able to move from the bottom of tube 2 through the smaller orifice 5 intermittently, the adjacent compartment contains serum only and does not return serum to the bottom of tube 3, That is to say that once serum is forced through filter 6 it must be contained in the compartment that communicates with said filter and must not return to mix with cells. In other words the bottom of the collection tube 2 containing clot, loose cells and serum serve as a storage reservoir for the smaller cellular compartment. Thus when the entire assembly is tilted, cells must be free to move quickly through filter 5 in the direction of element 8 for subsequent dispensing. In this regard and as previously mentioned the extension of resilient element 3 by component 7 is thereby provided to keep the clot away from orifice 5 and thereby clogging or obstructing passage of free cells stored at the bottom of the collection tube 2.

A second embodiment of the invention would provide for a dispensing system of similar construction for blood that has already been separated into two tubes namely the collection tube which would contain clot, loose cells and serum, and a second tube being separately labeled and containing serum only. Two separate devices could be snapped or forced within the openings of the respective tubes and provided therein would be a venting and dispensing system similar to the above mentioned preffered embodiment with the exeption that the venting system would comprise a tubular element that ran longitudinally to the bottom of each separated component. However this would necessatate the use of the additional tube and the labeleling thereof. Integrity of specimen is not maintained as in the preffered embodiment.

I claim:

1. A blood separating device adapted for use with a blood centrifuge tube, said blood separating device comprising:
   an elongated tubular member of an outer diameter less than the inner diameter of said blood centrifuge tube, Partitioning means to longitudinally partition said elongated tubular member into a first compartment means and a second compartment means; said first compartment means being substantially larger than said second compartment means,
   first vent means communicating with said first compartment means for venting air therefrom,
   second vent means communicating with said second compartment means, for venting air therefrom,
   first dispensing means communicating with said first compartment means at the first end of said elongated tubular member, for dispensing drops from said first compartment means,
   second dispensing means communicating with said second compartment means at the first end of said elongated tubular member, for dispensing drops from said second compartment means; said first and second dispensing means being so designed to enable dispensing from only one of said first and second compartment means at a time,
   resilient element means fitted in sealing relationship with the second end of said elongate tubular member and said partitioning means, said resilient element means further comprising first filter means communicating with said first compartment means, second filter means communicating with said second compartment means, and flange means designed to sealingly engage with the inner wall of said blood centrifuge tube.

2. The blood separating device of claim 1, wherein the flange means of said resilient element means acts as an air trap by trapping air within said blood centrifuge tube by forming a seal with the inner wall of said blood centrifuge tube against the outside environment.

3. The blood separating device of claims 1 or 2, wherein said first and second filter means are disposed within respective first and second orifice means in said resilient element means.

4. The blood separating device of claim 3, wherein said first filter means is designed to allow only blood serum to pass therethrough, and said second filter means being designed to allow blood serum and blood cells to pass therethrough.

5. The blood separating device of claim 1, wherein said first and second dispensing means each comprise a tubular member substantially smaller in diameter than said elongated tubular member.

6. The blood separating device of claim 1, wherein said resilient element comprises an extension means which prevents blood clots from obstructing said first and second filter means.

* * * * *